United States Patent [19]

Seki et al.

[11] Patent Number: 5,434,322
[45] Date of Patent: Jul. 18, 1995

[54] PROCESS FOR PREPARING 1,1-DICHLORO-2,2,2-TRIFLUOROETHANE

[75] Inventors: Eiji Seki; Satoshi Koyama, both of Osaka, Japan

[73] Assignee: Daikin Industries, Ltd., Osaka, Japan

[21] Appl. No.: 78,300

[22] PCT Filed: Oct. 29, 1992

[86] PCT No.: PCT/JP92/01398

§ 371 Date: Jun. 25, 1993

§ 102(e) Date: Jun. 25, 1993

[87] PCT Pub. No.: WO93/09080

PCT Pub. Date: May 13, 1993

[30] Foreign Application Priority Data

Oct. 30, 1991 [JP] Japan .................... 3-284555

[51] Int. Cl.$^6$ ............................. C07C 21/18
[52] U.S. Cl. ................................. 570/176
[58] Field of Search ......................... 570/176

[56] References Cited

FOREIGN PATENT DOCUMENTS

| 135722 | 3/1970 | Czech Rep. |
| 164954 | 5/1985 | European Pat. Off. |
| 3619079 | 12/1986 | Germany .............. 570/176 |
| 58-222038 | 12/1983 | Japan . |
| 1149739 | 12/1989 | Japan . |
| 1319440 | 12/1989 | Japan . |
| 1319441 | 12/1989 | Japan . |
| 9105752 | 5/1991 | WIPO .............. 510/176 |
| 9309080 | 10/1992 | WIPO .............. 570/176 |

*Primary Examiner*—Alan Siegel
*Attorney, Agent, or Firm*—Birch, Stewart, Kolasch & Birch

[57] ABSTRACT

A process for preparing 1,1-dichloro-2,2,2-trifluoroethane characterized in that 1,1,1-trichloro-2,2,2-trifluoroethane is reduced with hydrogen in the presence of a hydrogenating catalyst comprising platinum to which at least one metal selected from the group consisting of silver, copper, gold, tellurium, zinc, chromium, molybdenum and thallium is added.

1,1-Dichoro-2,2,2-trifluoroethne can be obtained in a high yield.

17 Claims, No Drawings

PROCESS FOR PREPARING 1,1-DICHLORO-2,2,2-TRIFLUOROETHANE

This application is a 371 of PCT/JP 92/01398, filed Oct. 29, 1992.

FIELD OF THE INVENTION

The pressent invention relates to a process for preparing 1,1-dichloro-2,2,2-trifluoroethane (HCFC123) which is a useful compound as a coolant, blowing agent or solvent and a raw material for compounds such as trifluoroacetic acid, HCFC124 (1-chloro-1,2,2,2-tetrafluoroethane), HFC125 (pentafluoroethane), etc.

DESCRIPTION OF THE PRIOR ART

It is known that 1,1-dichloro-2,2,2-trifluoroethane is synthesized by reducing 1,1,1-trichoro-2,2,2-trifluoroethane with, for example, zinc as a reducing agent in a protic solvent (cf. Japanese Patent Kokai Publication No. 222038/1983), with potassium acetate in the presence of an alcohol (cf. Czechoslovakia Patent No. 135722), or with sodium amalgam (cf. EP Patent No. 164954). However, all these reducing methods mentioned above have disadvantages that they are difficult to control and expensive. There are also kown methods in which reduction is effected with hydrogen in the presence of a hydrogenating catalyst (cf. Japanese Patent Kokai Publication Nos. 149739/1989, 319440/1989 and 319441/1989). The methods, however, give poor yields of 1,1-dichloro-2,2,2-trifluoroethane and hence are not the preffered methods for preparing it industrially.

SUMMARY OF THE INVENTION

It is an object of the present invention to provide a process for preparing 1,1-dichloro-2,2,2-trifluoroethane by catalytic reduction which does not cause the problems mentioned above.

Accordingly the present invention relates to a process for preparing 1,1-dichloro-2,2,2-trifluoroethane characterized in that 1,1,1-trichloro-2,2,2-trifluoroethane is reduced with hydrogen in the presence of a hydrogenating catalyst comprising platinum carried on a support to which at least one metal selected from the group consisting of silver, copper, gold, tellurium, zinc, chromium, molybdenum and thallium is added, to form 1,1-dichloro-2,2,2-trifluoroethane.

In reduction of 1,1,1-trichloro-2,2,2-trifluoroethane, particulary, in catalytic reduction, the chlorine atoms in a molecule tend to be reduced to an excess extent, resulting in a poor yield of 1,1-dichloro-2,2,2-trifluoroethane. Therefore, the inventors of the present invention have made diligent studies of methods by which only one chlorine atom in a molecule of the starting compound can be reduced and found that the intended product can be obtained in a high selectivity and a high yield by carrying out the hydrogenation reaction in the presence of an alloy catlyst comprising platinum.

DETAILED DESCRIPTION OF THE INVENTION

According to the present invention, it is important to add other metal to a platinum catalyst. In general, it is said that, in an alloy catalyst, the characteristics of component metal elements are developed depending on a composition of the alloy. The other metal is added to platinum in an amount of from 0.01 to 500% by weight, preferably from 0.1 to 300% by weight, based on the weight of platinum, to make the most of the features of platinum.

Although the concentration of an alloy which is held on a support can vary in the wide range of from 0.05 to 5% by weight based on the weight of the support, the concentration of from 0.5 to 2% by weight can be recommended.

Suitable supports used in the present invention include activated carbon, alumina, zirconia, titania, etc.

While a particle size of the support gives less effect on the reaction, it is preferably in the range of from 0.1 to 100 mm.

In the reduction of 1,1,1-trichloro-2,2,2-trifluoroethane, the ratio of hydrogen to the starting material can vary in a wide range. Usually a stoichiometric amount of hydrogen is used to remove a halogen atom. However, hydrogen may be used in much more than the stoichiometric amounts, for example, in an amount of 4 moles or more per one mole of the starting materials.

The reaction is carried out at or above atmospheric pressure. The reaction temperature is in the range of from 0° to 450° C., preferably from 50° to 300° C.

It is appropriate to carry out the reaction in a gas phase or a liquid phase. In the case of the gas phase reaction, the contact time is usually from 0.1 to 300 sec, particularly from 1 to 30 sec.

EXAMPLES

The present invention will be illustrated by means of examples hereinafter.

Example 1

To a platinum catalyst containing 0.5% by weight of the platinum held on activated carbon, an aqueous solution of $CuCl_2$ which amount corresponds to 1% by weight of the activated carbon was added, followed by the dropwise addition of 0.2 ml of formalin. The resulting mixture was aged at a temperature of 50° C. for 5 hours. Then water in it was distilled off under a reduced pressure and the residue was dried at 100° C. for a day.

18 cc of the catalyst thus prepared was packed in a SUS 316 reaction tube of 2 cm in inner diameter and 40 cm in length and the tube was heated by an electric furnace while passing nitrogen gas therethrough. After the predetermined temperature was reached, the nitrogen flow was stopped and 1,1,1-trichloro-2,2,2-trifuoroethane which had been previously vaporized and hydrogen gas were introduced in the tube at rates of 22 cc/min. and 44 cc/min., respectively. The reaction temperature was 110° C.

The resulting gas mixture was washed with water and dried over calcium chloride. Then it was analyzed by gas chromatography. The results are given in Table 1.

Example 2

In the similar method to that in Example 1, an alloy catalyst containing 0.1% by weight of silver on the platinum catalyst in which 0.5% by weight of platinum had been held on activated carbon was prepared using $AgNO_3$ and the reaction was carried out. The results are given in Table 1.

Example 3

In the similar method to that in Example 1, an alloy catalyst containing 0.1% by weight of tellurium on a platinum catalyst in which 0.5% by weight of platinum had been held on activated carbon was prepared using TeCl$_2$ and hydrogen chloride, and the reaction was carried out. The results are given in Table 1.

Example 4

In the similar method to that in Example 1, an alloy catalyst containing 0.1% by weight of gold on the platinum catalyst in which 0.5% by weight of platinum had been held on activated carbon was prepared using AuCl$_3$ and the reaction was carried out. The results are given in Table 1.

Example 5

In the similar method to that in Example 1, an alloy catalyst containing 2% by weight of zinc on the platinum catalyst in which 0.5% by weight of platinum had been held on activated carbon was prepared using ZnCl$_2$.

16.5 cc of the alloy catalyst thus prepared was packed in a SUS 316 reaction tube of 2 cm in inner diameter and 40 cm in length, and the tube was heated by an electric furnace while passing nitrogen gas therethrough. After the predetermined temperature was reached, the nitrogen flow was stopped and 1,1,1-trichloro-2,2,2-trifuoroethane which had been previously vaporized and hydrogen gas were introduced in the tube at rates of 12 cc/min. and 44 cc/min., respectively. The reaction temperature was 110° C.

The resulting gas mixture was washed with water and dried over calcium chloride. Then it was analyzed by gas chromatography. The results are given in Table 1.

Example 6

In the similar method to that in Example 1, an alloy catalyst containing 2% by weight of chromium on the platinum catalyst in which 0.5% by weight of platinum had been held on activated carbon was prepared using Cr(NO$_3$)$_3$.9H$_2$O.

16 cc of the alloy catalyst thus prepared was packed in a SUS 316 reaction tube of 2 cm in inner diameter and 40 cm in length, and the tube was heated by an electric furnace while passing nitrogen gas therethrough. After the predetermined temperature was reached, the nitrogen flow was stopped and 1,1,1-trichloro-2,2,2-trifuoroethane which had been previously vaporized and hydrogen gas were introduced in the tube at rates of 32.8 cc/min. and 65.8 cc/min., respectively. The reaction temperature was 130° C.

The resulting gas mixture was washed with water and dried over calcium chloride. Then it was analyzed by gas chromatography. The results are given in Table 1.

Example 7

In the similar method to that in Example 1, an alloy catalyst containing 2% by weight of thallium on the platinum catalyst in which 0.5% by weight of platinum had been held on activated carbon was prepared using TlCl$_3$.

13 cc of the alloy catalyst thus prepared was packed in a SUS 316 reaction tube of 2 cm in inner diameter and 40 cm in length and the tube was heated by an electric furnace while passing nitrogen gas therethrough. After the predetermined temperature was reached, the nitrogen flow was stopped and 1,1,1-trichloro-2,2,2-trifuoroethane which had been previously vaporized and hydrogen gas were introduced to the tube at rates of 18.4 cc/min and 36.7 cc/min, respectively. The reaction temperature was 130° C.

The resulting gas mixture was washed with water and dried over calcium chloride. Then it was analyzed by gas chromatography. The results are given in Table 1.

Example 8

In the similar method to that in Example 1, an alloy catalyst containing 2% by weight of molybdenum on the platinum catalyst in which 0.5% by weight of platinum had been held on activated carbon was prepared using (NH$_4$)$_6$Mo$_7$O$_{24}$.4H$_2$O.

14.5 cc of the alloy catalyst thus prepared was packed in a SUS 316 reaction tube of 2 cm in inner diameter and 40 cm in length and the tube was heated by an electric furnace while passing nitrogen gas therethrough. After the predetermined temperature was reached, the nitrogen flow was stopped and 1,1,1-trichloro-2,2,2-trifluoroethane which had been previously vaporized and hydrogen gas were introduced to the tube at rates of 33.2 cc/min. and 66.3 cc/min., respectively. The reaction temperature was 200° C.

The resulting gas mixture was washed with water and dried over calcium chloride. Then it was analyzed by gas chromatography. The results are given in Table 1.

TABLE 1

| Example No. | Conversion of 113a (%) | Selectivity of 123 (%) |
| --- | --- | --- |
| 1 | 94 | 91 |
| 2 | 97 | 96 |
| 3 | 87 | 86 |
| 4 | 93 | 90 |
| 5 | 55 | 93 |
| 6 | 86 | 85 |
| 7 | 42 | 92 |
| 8 | 50 | 96 |

What is claimed is:

1. A process for preparing 1,1-dichloro-2,2,2-trifluoroethane wherein 1,1,1-trichloro-2,2,2-trifluoroethane is reduced with hydrogen in the presence of a hydrogenating catalyst comprising an alloy of platinum and at least one metal selected from the group consisting of silver, copper, gold, tellurium, zinc, chromium, molybdenum and thallium, to form 1,1-dichloro-2,2,2-trifluoroethane.

2. The process according to claim 1, wherein said metal is silver.

3. The process according to claim 1, wherein said metal is copper.

4. The process according to claim 1, wherein said metal is gold.

5. The process according to claim 1, wherein said metal is tellurium.

6. The process according to claim 1, wherein said metal is zinc.

7. The process according to claim 1, wherein said metal is chromium.

8. The process according to claim 1, wherein said metal is molybdenum.

9. The process according to claim 1, wherein said metal is thallium.

10. The process according to claim 1, wherein said metal is added to platinum in an amount from 0.01 to 500% by weight.

11. The process according to claim 1, wherein said hydrogenating catalyst comprises an alloy of platinum and said added metal on a support, at a concentration of from 0.5 to 2% by weight of said alloy, based on the weight of said support.

12. The process according to claim 1, wherein said hydrogenating catalyst is in the form of particles in the size range of from 0.1 to 100 mm.

13. The process according to claim 1, wherein the ratio of hydrogen to 1,1,1-trichloro-2,2,2-trifluoroethane may vary from stoichiometric to a 4:1 molar ratio, respectively.

14. The process according to claim 1, wherein the reaction temperature may vary from 0°–450° C.

15. The process according to claim 1, wherein the 1,1,1-trichloro-2,2,2-trifluoroethane is in the gas phase.

16. The process according to claim 1, wherein the 1,1,1-trichloro-2,2,2-trifluoroethane is in the liquid phase.

17. A process for preparing 1,1-dichloro-2,2,2-trifluoroethane comprising:
  reducing 1,1,1-trichloro-2,2,2-trifluoroethane with hydrogen in the presence of a hydrogenating catalyst, comprising an alloy of platinum with at least one other metal selected from the group consisting of silver, copper, gold, tellurium, zinc, chromium, molybdenum and thallium;
  wherein the temperature of the reaction is from 0°–450° C.; the amount of said other metal, relative to said platinum, is from 0.01 to 500% by weight; the amount of said alloy on a support therefor is from 0.5 to 2% by weight, relative to said support; and the hydrogen is present in at least a stoichiometric amount, relative to said 1,1,1-trichloro-2,2,2-trifluoroethane.

* * * * *